(12) United States Patent
Manninen

(10) Patent No.: US 9,308,030 B2
(45) Date of Patent: Apr. 12, 2016

(54) DEROTATION APPARATUS FOR TREATING SPINAL IRREGULARITIES

(71) Applicant: GLOBUS MEDICAL, INC., Audubon, PA (US)

(72) Inventor: Katherine Manninen, Limerick, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 270 days.

(21) Appl. No.: 13/908,459

(22) Filed: Jun. 3, 2013

(65) Prior Publication Data

US 2014/0052191 A1    Feb. 20, 2014

Related U.S. Application Data

(62) Division of application No. 12/632,445, filed on Dec. 7, 2009, now Pat. No. 8,475,467.

(51) Int. Cl.
*A61F 2/46* (2006.01)
*A61B 17/70* (2006.01)

(52) U.S. Cl.
CPC .................. *A61B 17/7079* (2013.01)

(58) Field of Classification Search
CPC ............ A61B 17/708; A61B 17/7077; A61B 17/7079; A61B 17/60; A61B 17/6408; A61B 17/6416; A61B 17/6441; A61B 17/645; A61B 17/6458; A61B 17/6466
USPC ......... 606/86 A, 96, 104–105, 246, 279, 914, 606/916
See application file for complete search history.

(56) References Cited

U.S. PATENT DOCUMENTS

| | | | |
|---|---|---|---|
| 5,649,931 A | 7/1997 | Bryant et al. | |
| 2004/0147937 A1 | 7/2004 | Dunbar | |
| 2006/0271050 A1 | 11/2006 | Piza Vallespir | |
| 2007/0161987 A1* | 7/2007 | Capote et al. ................... | 606/61 |
| 2007/0213716 A1 | 9/2007 | Lenke | |
| 2008/0015601 A1 | 1/2008 | Castro | |
| 2009/0228053 A1 | 9/2009 | Kolb | |
| 2011/0137358 A1 | 6/2011 | Manninen | |

FOREIGN PATENT DOCUMENTS

WO      2010065729 A2    6/2010

OTHER PUBLICATIONS

International Preliminary Report on Patentability and Written Opinion for PCT/US2012/060702 dated Apr. 22, 2014.

* cited by examiner

*Primary Examiner* — David Bates
*Assistant Examiner* — Olivia C Chang

(57) ABSTRACT

Treatment of spinal irregularities, including, in one or more embodiments, derotation apparatus and systems that can be used to reduce the rotation of vertebral bodies. Derotation apparatus that may comprise a tube assembly comprising an inner sleeve and an outer sleeve disposed over the inner sleeve. The inner sleeve may have a distal end for attachment to an implant. The tube assembly may further comprise a handle assembly. The tube assembly may further comprise a ball joint assembly disposed between the tube assembly and the handle assembly. The ball joint assembly may comprise a ball joint configured for attachment to a coupling rod.

16 Claims, 7 Drawing Sheets

DEROTATION APPARATUS FOR TREATING SPINAL IRREGULARITIES

CROSS REFERENCE TO RELATED APPLICATIONS

The present application is a divisional application of U.S. patent application Ser. No. 12/632,445 filed on Dec. 7, 2009, which is incorporated in its entirety herein.

FIELD OF THE INVENTION

The present disclosure generally relates to treatment of spinal irregularities. In particular, in one or more embodiments, the present disclosure relates to derotation apparatus and systems that can be used to reduce the rotation of vertebral bodies

BACKGROUND

Many types of spinal irregularities can cause pain, limit range of motion, or injure the nervous system within the spinal column. These irregularities can result from, without limitation, trauma, tumor, disc degeneration, and disease. By way of example, scoliosis and kyphosis are irregularities that can result in a complex, three-dimensional problem with lateral curvature of the spine and segmental vertebral rotation. Advances in medicine and engineering have provided doctors with a plurality of devices and techniques for correcting these deformities or irregularities.

One technique for treating scoliosis is the Harrington rod. The Harrington rod operates on a distraction system attached by hooks to the spine that when distracted, straightens the curve in the spine. Until the 1970's, the Harrington rod was the preferred method of treatment for scoliosis. Follow-up studies of these rods documented the negative effects of using distraction rods alone for correction of spinal deformities, including "flat back syndrome" and the resulting degenerative changes in the lower lumbar spine. Other methods of management, including spinal fixations systems that include segmental wires, hooks, rods and/or bone fasteners (e.g., pedicle screws) have revolutionized the treatment of spinal deformities. The advent and availability of smaller and stronger bone fasteners has further advanced treatment, allowing for effective application of corrective forces to posterior systems into the high thoracic spine.

Until recently, spinal fixation systems comprising bone fasteners and rods were used almost exclusively to correct the lateral curvature of the spine, with little attention paid to segmental vertebral derotation, primarily because bone fastener instrumentation did not provide a means of rotating the individual vertebral bodies. These systems focused on reducing the rod into the bone fasteners and using rod grips and/or in situ benders to translate the rod to restore sagittal and coronal plane balance. While these patients appear to be corrected on an A-P or lateral x-ray, they frequently present with pronounced rib hump, or axial twisting of the spine, which can result in significant pulmonary compromise and further degenerative changes in the spine.

Techniques have also been developed to address segmental vertebral rotation caused by irregularities, such as scoliosis. For instance, derotation systems have been used for the treatment of segmental vertebral rotation. Current derotation systems typically include a tube or series of tubes that slot over the implant (e.g., pedicle screw) much like a counter torque. These tubes allow the surgeon to push on and rotate the vertebral bodies away from the instrumentation, which when applied to the apex of the deformity, will straighten the lateral curvature and can reduce some of the individual rotation between bodies. However, this maneuver frequently results in flat back syndrome and, more importantly, very high applied forces to individual screws, which can lead to bone fasteners breaching the medial or lateral walls of the pedicle. This leads to loss of fixation at these levels and can result in paralysis if the breached screws impact the spinal cord. To reduce the force applied to any one screw, derotation systems may link multiple screws together so that the force of correction is applied over multiple screws. However, the surgeon typically cannot connect more than two tubes, and the process to connect the tubes is time consuming, confusing, and often requires separate instruments to assemble and tighten the system together. These factors in an already long and complex deformity case have limited the impact of derotation systems for posterior spinal fusion procedures.

Thus, there is a need for improved derotation systems that can securely connect to implants with efficient coupling to multiple implants.

SUMMARY

An embodiment of the present invention includes a derotation apparatus. The derotation apparatus may comprise a tube assembly comprising an inner sleeve and an outer sleeve disposed over the inner sleeve. The inner sleeve may have a distal end for attachment to an implant. The tube assembly may further comprise a handle assembly. The tube assembly may further comprise a ball joint assembly disposed between the tube assembly and the handle assembly. The ball joint assembly may comprise a ball joint configured for attachment to a coupling rod.

The features and advantages of the present invention will be readily apparent to those skilled in the art. While numerous changes may be made by those skilled in the art, such changes are within the spirit of the invention.

DETAILED DESCRIPTION OF THE ILLUSTRATED EMBODIMENTS

Figure 1:
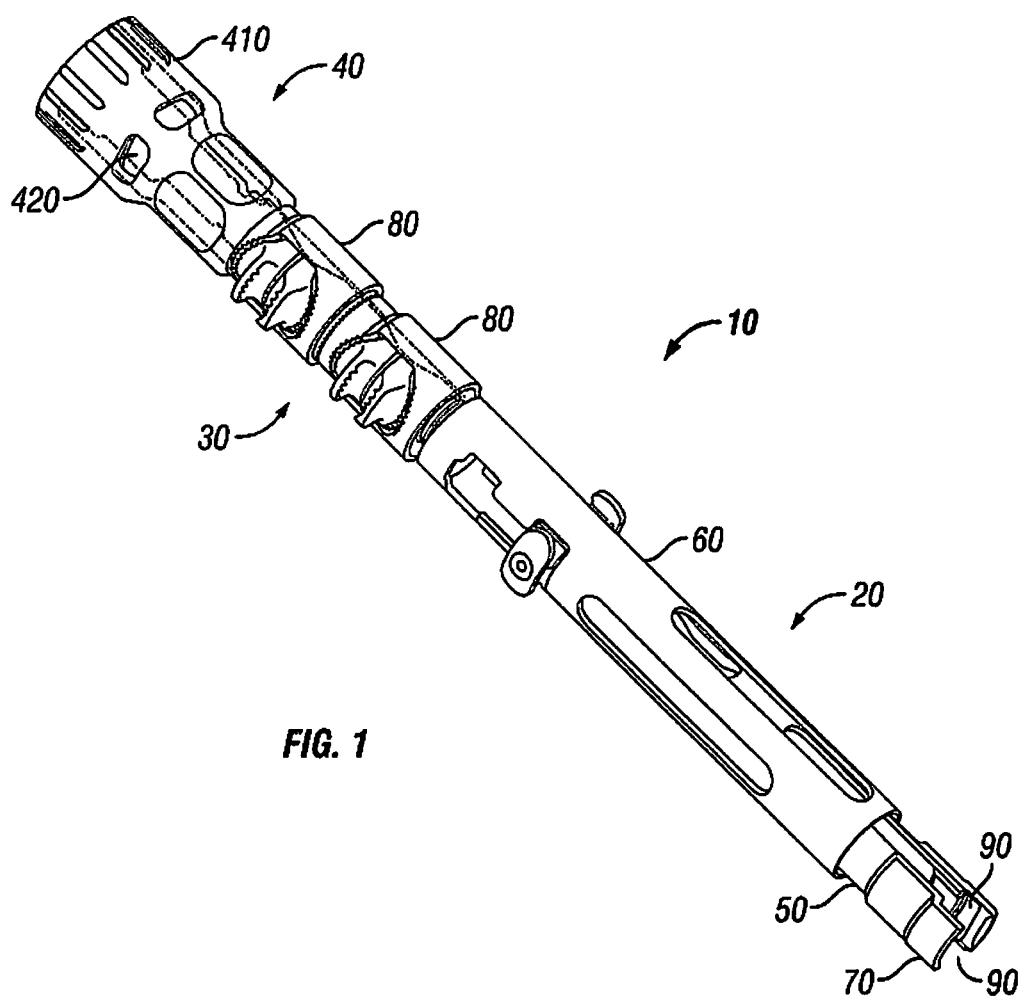
FIG. 1 illustrates a derotation apparatus in accordance with one embodiment of the present invention.
Figure 2:
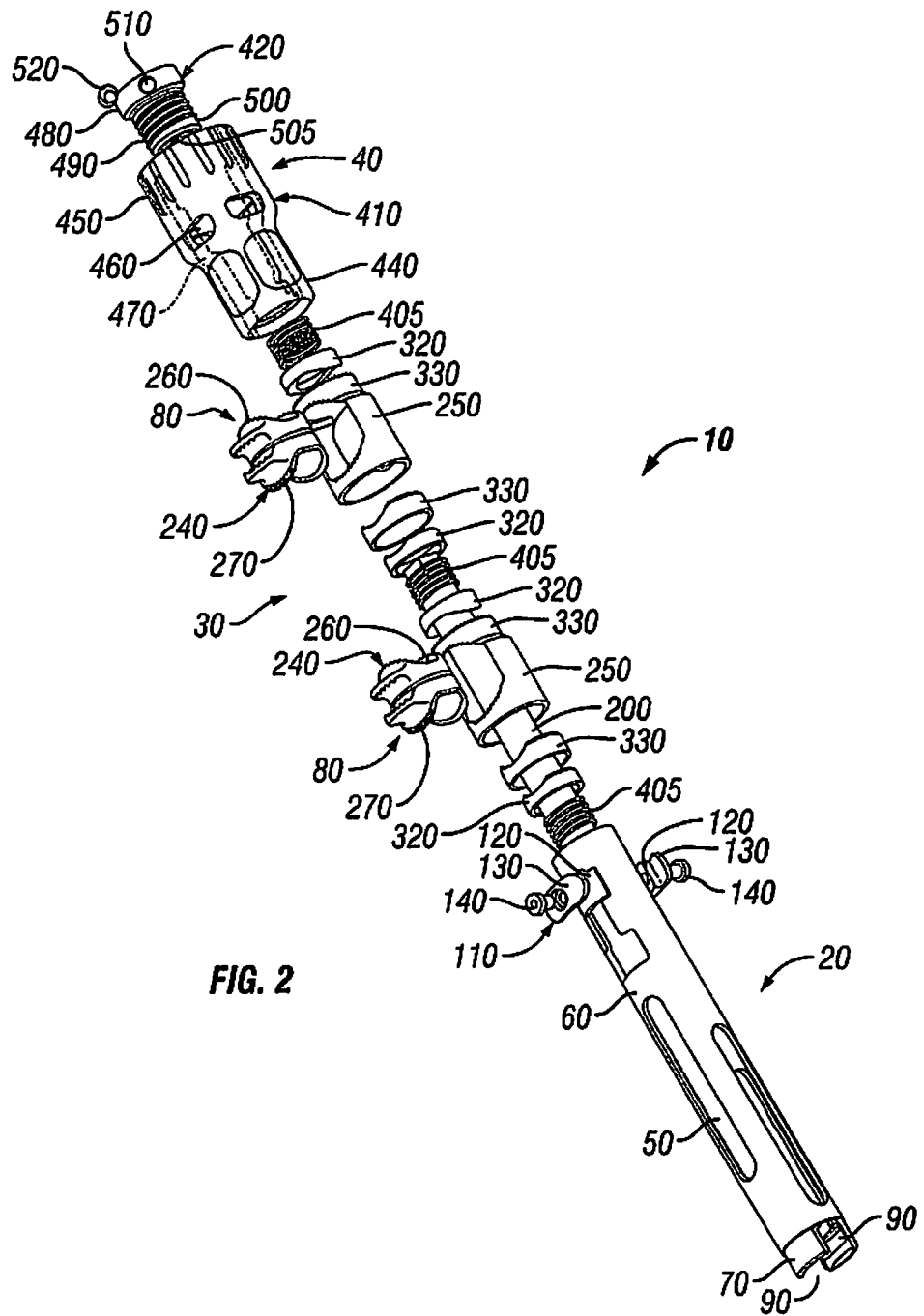
FIG. 2 illustrates an exploded view of a derotation apparatus in accordance with one embodiment of the present invention.

FIGS. 1 and 2 illustrate a derotation apparatus 10 in accordance with an embodiment of the present invention. As illustrated, derotation apparatus 10 comprises a tube assembly 20, a ball joint assembly 30, and a handle assembly 40. Tube assembly 20 may comprise an inner sleeve 50 and an outer sleeve 60 disposed over inner sleeve 50 with inner sleeve 50 having a distal end 70 configured and adapted for attachment to an implant (not illustrated). In an embodiment, the implant may be attached to a vertebral body. Ball joint assembly 30 may comprise at least one ball joint 80. As illustrated, ball joint assembly comprises two ball joints 80. As will be discussed in more detail below, force may be applied to handle assembly 40 to derotate the vertebral body to which the implant is attached. This should result in reducing the rotation between vertebral bodies in a patient's spine. In addition, rotation of the vertebral bodies may also straighten curvature of the spine.

Figure 3:
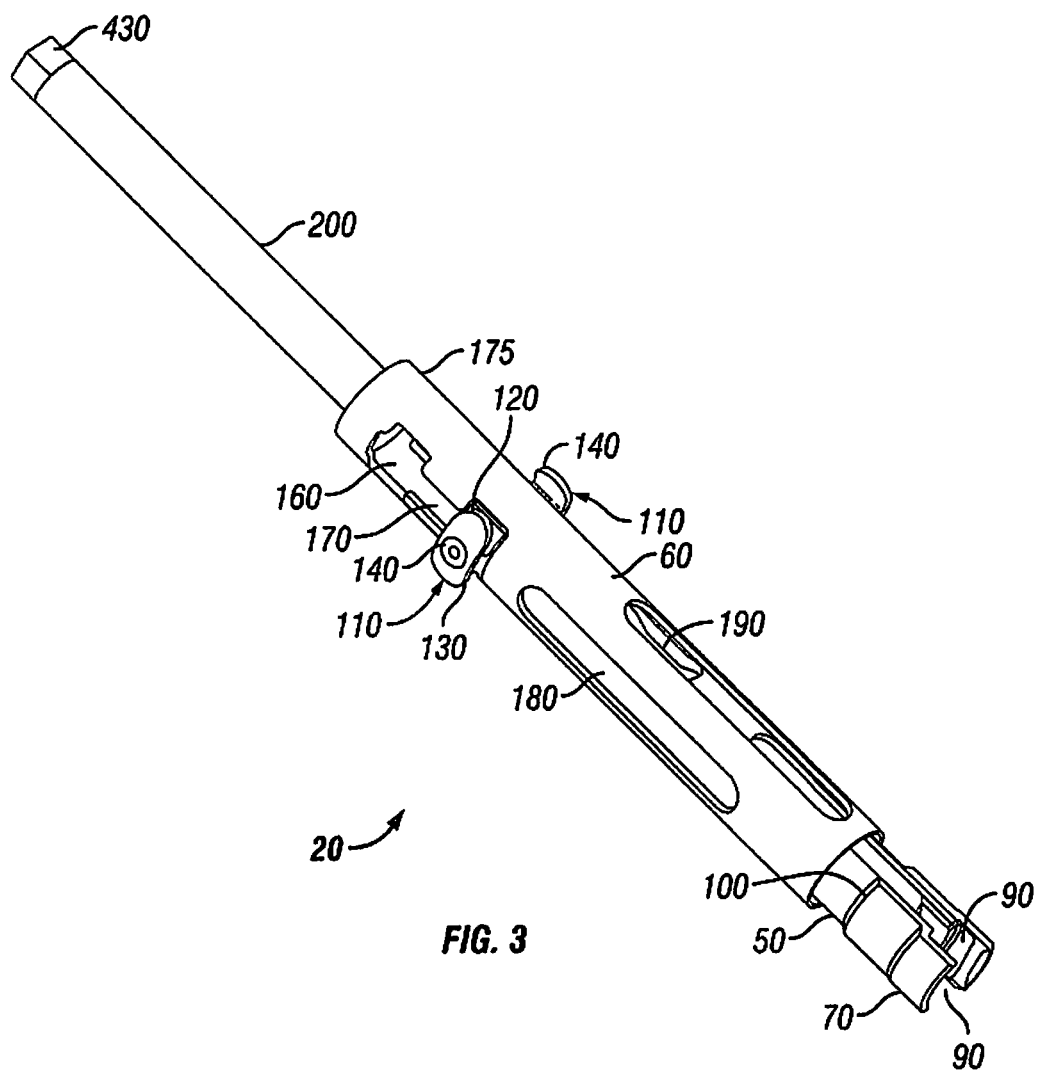
FIG. 3 illustrates an embodiment of a tube assembly of a derotation apparatus.

Referring now to FIGS. 1-5, tube assembly 20 of derotation apparatus 10 will be described in more detail in accordance with one embodiment of the present invention. FIG. 3 illustrates tube assembly 20 with ball joint assembly 30 and handle assembly 40 removed. In general, tube assembly 20 should attach derotation apparatus 10 to the implant (not illustrated). As previously mentioned, tube assembly 20 includes inner sleeve 50 and outer sleeve 60 disposed over inner sleeve 50.

Inner sleeve 50 includes distal end 70 configured and adapted for attachment to an implant (not illustrated). In an embodiment (not illustrated), distal end 70 fits over at least a portion of an implant. While not illustrated, the inner surfaces of distal end 70 may include features configured and adapted for attachment to the implant. For example, distal end 70 may include a connection that when allows for coupling the inner sleeve 50 to the implant by applying some force. In another embodiment, a dovetail-type connection, such that placement of distal end 70 over the implant with rotation should couple the inner sleeve 50 to the implant, thus preventing separation. Other suitable mechanisms may be used to prevent separation of distal end 70 from the implant. The implant may include any of a variety of surgical implants that may be secured to a vertebral body, including, for example, a spine stabilization system that includes a bone fastener (e.g., a pedicle screw) coupled to a rod. By way of example, distal end 70 may fit over the head of the bone fastener. Distal end 70 may include slots 90 through which the rod extends when distal end 70 is fitted over the bone fastener, for example. Distal end 70 may further include a beveled surface 100.

Inner sleeve 50 may further include locking mechanisms 110 that extend radially from inner sleeve 50 opposite distal end 70. Locking mechanisms 110 may each include a stop 120, actuator 130, and guide 140. As illustrated, the stop 120 and actuator 130 may be on either end of the guide 140 with the guide 140, for example, being a pin or rod extending between stop 120 and actuator 130. Pressing down on actuator 130 should cause locking mechanisms 110 to depress towards inner sleeve 50.

Referring now to FIGS. 1-5, outer sleeve 60 will be described in more detail in accordance with one embodiment of the present invention. As previously mentioned, outer sleeve 60 may be disposed over inner sleeve 50. Outer sleeve 60 may comprise a first opening 150 and a second opening 160 connected by channel 170. While not illustrated, outer sleeve 60 further may comprise corresponding openings to first opening 150, second opening 160, and channel 170, on the opposite side of outer sleeve. First opening 150 and second opening 160 should each have a greater width than channel 170. Second opening 160 should be closer to proximal end 175 of outer sleeve 60 than first opening 150. Channel 170 should generally be dimensioned to allow passage of guide 140 of locking mechanisms 110, but should not be of sufficient size for passage of stop 120, when tube assembly 20 is assembled. First opening 150 and second opening 160 should be dimensioned to allow penetration of stop 120. Outer sleeve 60 further may comprise additional openings, such as third opening 180 and fourth opening 190. These additional openings should provide access to inner sleeve 50 after assembly of tube assembly 20, for example, so that interior components of tube assembly 20 may be inspected and/or cleaned as desired. In an embodiment, outer sleeve further comprises a chamfered distal end 210.

As illustrated by FIGS. 2 and 3, shaft 200 may be coupled to outer sleeve 60 in accordance with one embodiment of the present invention. In general, shaft 200 may extend axially from proximal end 175 of outer sleeve 60. In an embodiment, shaft 200 and outer sleeve 60 may be a unitary piece. In an alternative embodiment (not illustrated), shaft 200 may be attached to outer sleeve by any suitable mechanism, such as by a bolted and/or threaded connection. As illustrated, shaft may have a square-shaped proximal end 430. While proximal end 430 of shaft 200 is illustrated as generally square in shape other shapes (e.g., circular) may also be suitable in accordance with embodiments of the present invention.

Figure 4:
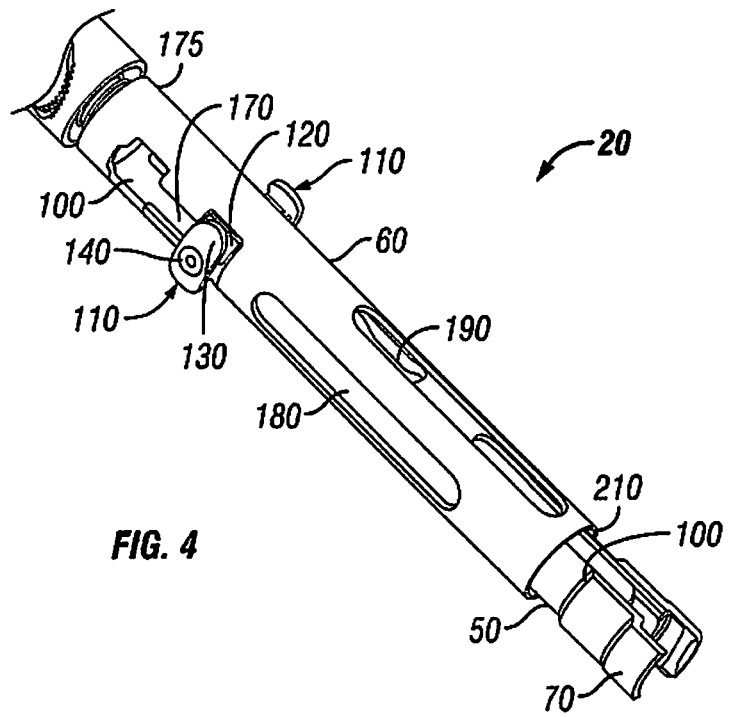
FIG. 4 illustrates an embodiment of a derotation apparatus with a tube assembly in an unlocked position.
Figure 5:
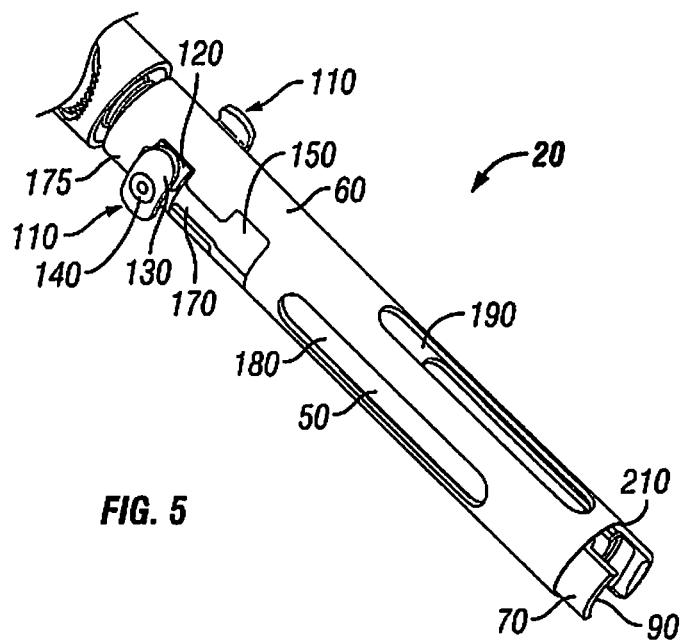
FIG. 5 illustrates an embodiment of a derotation apparatus with a tube assembly in a locked position in accordance with one embodiment of the present invention.

FIGS. 4 and 5 illustrate operation of the locking mechanisms 110 of tube assembly 20 in accordance with one embodiment of the present invention. As will be described below, locking mechanisms 110 may be used to couple derotation apparatus 10 to the implant (not illustrated). The following description is with respect to movement of one of locking mechanisms 110 from an unlocked to a locked position. However, it should be understood that the illustrated embodiment contains two locking mechanisms 110 with both locking mechanisms 110 functioning in a similar manner to effectuate locking and unlocking of tube assembly 20.

FIG. 4 illustrates tube assembly 20 with locking mechanism 110 in an unlocked position in accordance with one embodiment of the present invention. As illustrated, when tube assembly 20 is unlocked, outer sleeve 60 may be disposed over inner sleeve 50 with distal end 70 of inner sleeve 50 uncovered. In an embodiment, when unlocked, locking mechanism 110 should extend through first opening 150 in outer sleeve 60. Block 120 may be positioned in first opening 150 so that locking mechanism 110 is engaged with first opening 150, preventing movement of locking mechanism 110. This should fix the position of inner sleeve 50 with respect to outer sleeve 60. When in the unlocked position, distal end 70 of inner sleeve 50 may be placed over at least a portion of an implant (not illustrated). Various mechanism may be applied so that the derotation apparatus 10 is prevented from separating from the distal end 70 of the implant.

FIG. 5 illustrates tube assembly 20 with locking mechanism 110 in a locked position in accordance with one embodiment of the present invention. The tube assembly 20 may be placed in the locked position to further secure the inner sleeve 50 onto the implant. To place the locking mechanism 110 in a locked position in accordance with one embodiment, actuator 130 should be pressed causing locking mechanism 110 to depress towards inner sleeve 50. Stop 120 may move completely through first opening 150 so that stop 120 disengages with first opening 150. With locking mechanism 110 depressed, pressure should be applied to tube assembly 20 forcing outer sleeve 60 further down onto inner sleeve 50. As outer sleeve 60 passes down onto inner sleeve 50, guide 140 should pass through channel 170 until locking mechanism 110 reaches second opening 160. Actuator 130 should then be released so that locking mechanism 110 raises and engages with second opening 160 with stop 120 preventing movement. As outer sleeve 60 is forced down onto first sleeve 50, chamfered distal end 210 of outer sleeve 60 passes over beveled surface 100. This forces the outer sleeve 60 against distal end 70 of inner sleeve 50 pressing distal end 70 tighter against the implant (not illustrated). This tightening force should clamp distal end 70 onto the implant preventing separation of distal end 70 from the implant. Accordingly, in this manner, derotation apparatus 10 can be securely connected to an implant. Other suitable mechanisms for securing derotation apparatus 10 onto an implant may also be used in accordance with embodiments of the present invention.

Figure 6:
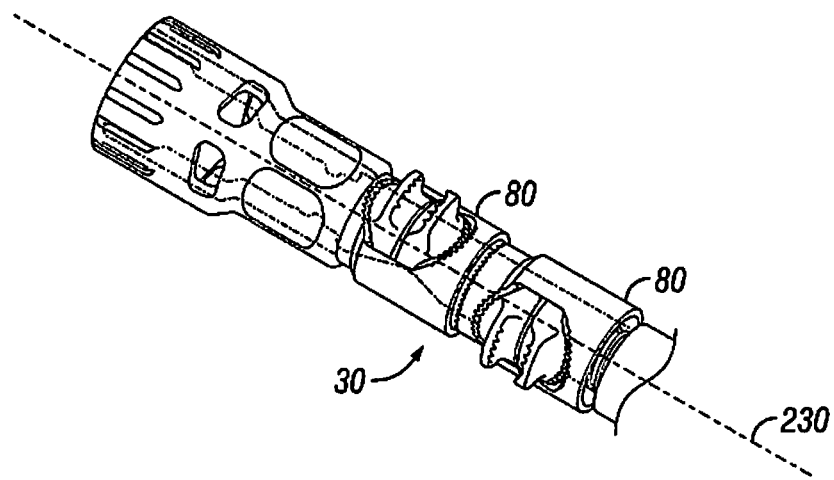
FIG. 6 illustrates an embodiment of a derotation apparatus with the ball joints at different rotational angles.
Figure 7:
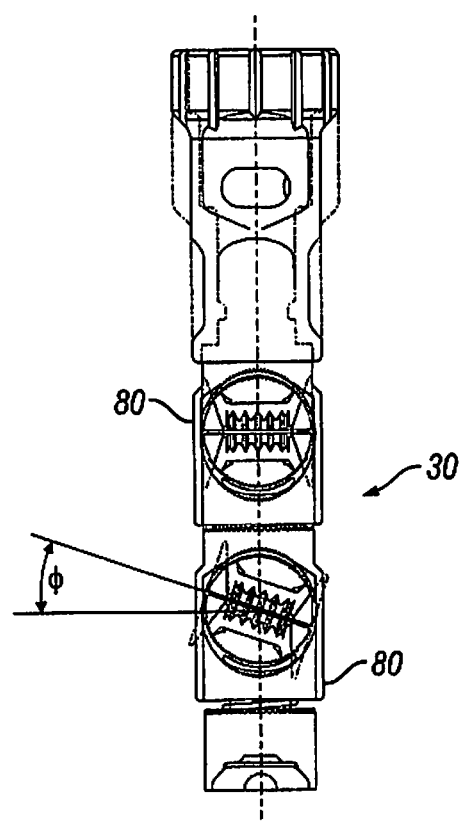
FIG. 7 illustrates an embodiment of a derotation apparatus with one of the ball joints oriented at an angled with respect to the derotation apparatus.

Derotation apparatus 10 may further comprise ball joint assembly 30. In general, ball joint assembly 30 should be configured and adapted to couple derotation apparatus 10 to least one additional derotation apparatus 10. As discussed below with respect to FIGS. 12-14, two or more derotation apparatuses 10 may be linked by at least one coupling rod 220 forming a coupled derotation system 225. Referring now to FIGS. 1 and 2, ball joint assembly 30 may comprise at least one ball joint 80. In an embodiment, at least one ball joint 80 may be a spring-loaded ball joint. In general, each of at least one ball joint 80 may be rotatable. For example, each of at least one ball joint 80 should be rotatable about at least one axis and, preferably, at least two axes. In an embodiment illustrated by FIG. 6, each of at least one ball joint 80 may be rotated about z-axis 230. For example, at least one ball joint 80 may rotate about z-axis 230 by an angle of up to about 360°. As illustrated, the two ball joints 80 may have an angle of rotation of about 90° with respect to one another. In an embodiment illustrated by FIG. 7, at least one ball joint 80 may be rotated about a y-axis (not illustrated), which would extend in a direction perpendicular to the figure. For example, at least one ball joint 80 may rotate about the y-axis by an angle (θ) of up to about 360°. As illustrated, one of the ball joints 80 may rotate about the y-axis by an angle (θ) of at least about 20°.

Figure 8:
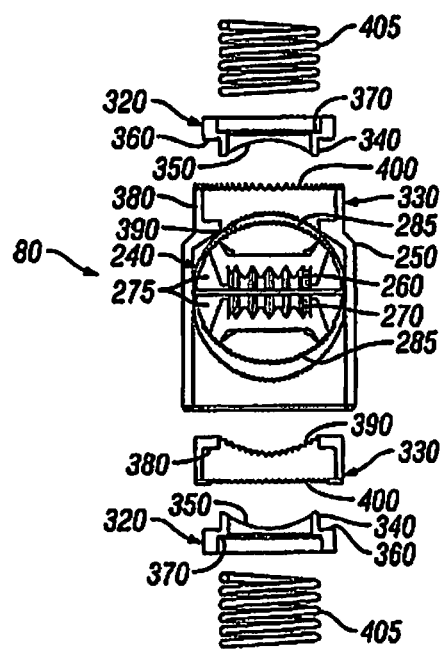
FIG. 8 illustrates an exploded front view of a ball joint in accordance with one embodiment of the present invention.
Figure 9:
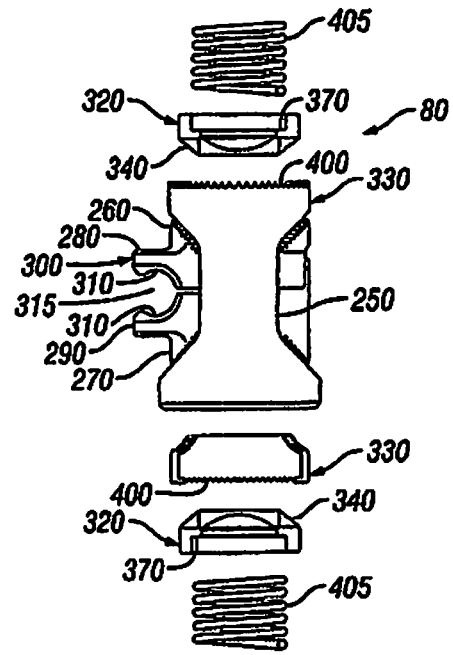
FIG. 9 illustrates an exploded side view of a ball joint in accordance with one embodiment of the present invention.

Referring now to FIGS. 2, 8 and 9, ball joint assembly 30 will be described in more detail with respect to one embodiment of the present invention. As illustrated, ball joint assembly 30 comprises at least one ball joint 80. Each ball joint 80 may comprise a ball 240 contained within a housing 250 with ball 240 and housing 250 disposed on shaft 200. In an embodiment, ball 240 is formed by upper portion 260 and lower portion 270 that when matched together form ball 240. Upper portion 260 and lower portion 270 may each be generally annularly shaped so that each portion can fit onto shaft 200. As illustrated, upper portion 260 may be a separate piece that forms the top half of ball 240 while lower portion 270 may be a separate piece that forms the lower half of ball 240. In an embodiment (not illustrated), upper portion 260 and lower portion 270 are unitary pieces or, alternatively, coupled in some manner. Each of upper portion 260 and lower portion 270 may comprise a hole, such as tapered through hole 275 to, for example, facilitate rotation of at least one ball joint 80 on shaft 200. In an embodiment, upper portion 260 and lower portion 270 of each ball joint 80 may comprise serrated ball edges 285 on at least a portion of their respective exterior surfaces forming the outer surface of respective ball 240.

In the illustrated embodiment, each of upper portion 260 and lower portion 270 comprises a tab, for example, upper tab 280 and lower tab 290. Upper tab 280 and lower tab 290 may extend radially and outwardly from upper portion 260 and lower portion 270, respectively. Together the upper tab 280 and lower tab 290 may be configured and adapted to form a clamp 300 that grips coupling rod 220 (illustrated on FIGS. 12-14). In this manner, each ball joint 80 may retain a corresponding coupling rod 220. In an embodiment, clamp 300 formed by upper tab 280 and lower tab 290 is open, for example, to facilitate insertion of coupling rod 220. In an embodiment, clamp 300 is generally u-shaped. As illustrated, the facing surfaces 310 of upper tab 280 and lower tab 290 may be rounded so that upper tab 280 and lower tab 290 form rod opening 315 for receiving coupling rod 220.

As illustrated by FIGS. 2, 8, and 9, each one ball joint 80 further may comprise inner washers 320 and outer washers 330 that are each disposed over shaft 200, in accordance with one embodiment of the present invention. Inner washers 320 and outer washers 330 may each comprise a central opening (not illustrated) that is dimensioned for shaft 200 to fit through. Inner washers 320 may each comprise a protruding rim 340 with a rounded surface 350. In an embodiment, rounded surface 350 may be smooth to allow for rotation of ball 240. Inner washers 320 also may each comprise an outer shoulder 360. As illustrated, outer shoulder 360 of each of inner washers 320 may be inwardly facing, in that outer shoulder 360 may face ball 240 of the respective ball joint 80. Inner washers 320 further may each comprise an inner spring shoulder 370 facing in the opposite direction of outer shoulder 360. Outer washers 330 may each comprise an inner shoulder 380. This inner shoulder 380 is outwardly facing because it faces away from ball 240. In an embodiment, one or more of outer washers 330 may be integral with housing 250. As illustrated by FIG. 8, this integral washer of outer washers 330 may be the uppermost of outer washers 330, in accordance with one embodiment. In an alternative embodiment (not illustrated), each of outer washers 330 may be separate pieces from housing 250. As illustrated by FIG. 9, the lowermost of outer washers 330 may be separate from housing 250 in accordance with one embodiment. In an embodiment, one or more of outer washers 330 may each comprise one or more serrated edges. In the illustrated embodiment, each of outer washers 330 may comprise inner serrated edge 390 and outer serrated edge 400. As illustrated, inner serrated edge 390 may be rounded for mating with ball 240.

Each ball joint 80 may further comprise springs 405. As illustrated, springs 405 may be disposed over shaft 200 on either side of inner washers 320. In an embodiment, springs 405 are compression springs. In an embodiment, each ball joint 80 may share one of springs 405. In the illustrated, embodiment, each ball joint 80 comprises two springs 80 with each ball joint sharing one of springs 80. In an alternative embodiment (not illustrated), each of at least one ball joint 80 may comprise one compression spring.

Referring now to FIGS. 1 and 2, handle assembly 40 will be described in more detail, in accordance with one embodiment of the present invention. In the illustrated embodiment, handle assembly 40 comprises handle 410 and cap 420. Handle 410 may be generally tubular in shape with a passageway extending longitudinally therethrough. As illustrated, handle 410 may comprise lower tubular section 440 and upper tubular section 450, in an embodiment, lower tubular section 440 may have an inner diameter than is smaller than the inner diameter of upper tubular section 450. In an embodiment (not illustrated), lower tubular section 440 may have inner threads. When derotation apparatus 10 is assembled, shaft 200 may be received into lower tubular section 440. One or more holes 460 may be formed in upper tubular section 440. Handle 410 further may comprise inner cap shoulder 470, for example, at the intersection of lower tubular section 440 and upper tubular section 450. As illustrated, interior cap shoulder 470 may be upwardly facing.

In an embodiment, cap 420 may be configured and adapted to lock handle 410 on derotation apparatus 10. As illustrated, cap 420 may comprise head 480, elongated shaft 490, and exterior threads 500. When derotation apparatus 10 is assembled, for example, cap 420 may be disposed in the interior of handle 410 with cap 420 engaging inner cap shoulder 470 of handle 410 and elongated shaft 490 extending down into lower tubular section 440. While not illustrated, cap 420 may include features to lock into handle 410. In an embodiment (not illustrated), cap 420 may be thread into lower tubular section 440 of handle 410. For example, exterior threads 500 of cap 420 may thread into interior threads (not illustrated) in lower tubular section 440. In addition, cap 420 may also include features to secure handle 410 and ball joint assembly 30 on shaft 200. For example, cap 420 may be disposed over proximal end 430 of shaft 200 with screw 520 inserted into threaded hole 510 of cap 420 to engage shaft 200. As illustrated, threaded hole 510 may be in head 480 of cap 420. In an embodiment, elongated shaft 490 may have a rectangularly shaped opening 505 into which square-shaped proximal end 430 of shaft 200 may be inserted. It should be understood that other shaped openings in elongated shaft 490 may also be suitable for use in embodiments of the present invention. With cap 420 secured onto shaft 200, handle 410 may be rotated to, for example, tighten handle 410 down onto shaft 200, thus tightening handle 410 down onto ball joint assembly 30. The preceding description describes handle assembly 40 that can be used in accordance with an embodiment of the present invention. However, it should be understood that other suitable assemblies for tightening down onto ball joint assembly 30 can be used in accordance with embodiments of the present invention.

Figure 10:
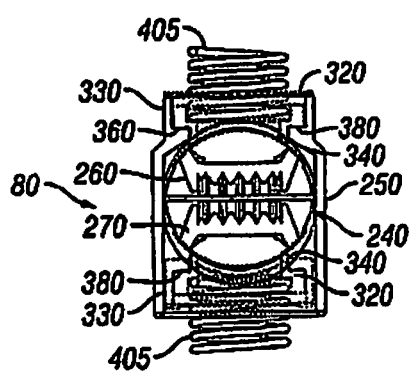
FIG. 10 illustrates an embodiment of a ball joint in an unlocked position in accordance with one embodiment of the present invention.

Referring now to FIG. 10, ball joint 80 is illustrated in an unlocked position in accordance with one embodiment of the present invention. As illustrated, outer washers 330 may be located on either side of ball 240. As previously described, ball 240 may be formed by upper portion 260 and lower portion 270 that match together to form ball 240. In the illustrated embodiment, the uppermost of outer washers 330 is integral with housing 250 with the lowermost of outer washers 330 slidably disposed within housing 250. Inner washers 320 may also be located on either side of ball 240. Outer shoulder 360 of each of inner washers 320 should engage corresponding inner shoulder 380 of outer washers 330. As illustrated, protruding rim 340 of each of inner washers 320 may extend through a corresponding one of outer washers 330. Rounded surface 350 of protruding rim 340 of each of inner washers 320 may contact ball 240. As previously mentioned, rounded surface 350 may be smooth to allow for rotation of ball 240. As illustrated, springs 405 may be located on either side of inner washers 320. In the illustrated embodiment, springs 405 engage inner spring shoulder 370 of inner washers 320. In an embodiment, springs 405 may force outer shoulder 360 of each inner washer 320 into engagement with inner shoulder 380 of each outer washer 330.

Figure 11:
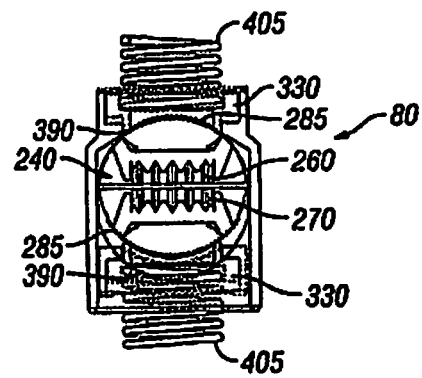
FIG. 11 illustrates an embodiment of a ball joint in a locked position in accordance with one embodiment of the present invention.

Referring now to FIG. 11, ball joint 80 is illustrated in a locked position in accordance with one embodiment of the present invention. Ball joint 80 may be placed in a locked position to secure coupling rod 220 in clamp 300 (illustrated on FIGS. 12-14). To place ball joint 80 in a locked position in accordance with one embodiment, handle assembly 40 may be tightened down onto ball joint assembly 30, for example. As the handle assembly 40 is tightened, inner washers 320 may be pushed inside of outer washers 330 so that protruding rim 340 no longer extends through outer washers 330. The outer washers 330 may then engage ball 240 with springs 405 forcing upper portion 260 and lower portion 270 together. By forcing upper portion 260 and lower portion 270 together, clamp 300 may be closed onto a coupling rod 220 (illustrated on FIGS. 12-14). In addition, engagement of outer washers 330 with ball 240 may also prevent rotation of ball 240. As previously mentioned, outer washers 330 and/or outer surfaces 240 of ball 240 may be serrated. In an embodiment, inner serrated edge 390 of each outer washer 330 engages serrated ball edges 285 to prevent rotation of ball 240. The preceding description describes one suitable technique for locking ball joint 80 to prevent rotation of ball 240 and secure coupling rod 220 in clamp 300. However, it should be understood that other suitable techniques for preventing rotation of ball 240 and for securing coupling rod 220 in clamp 300 can be used in accordance with embodiments of the present invention.

One or more derotation apparatuses 10 may be used in the treatment of spinal irregularities in accordance with embodiments of the present invention. For example, derotation apparatus 10 may be used to derotate a vertebral body, thus reducing rotation between vertebral bodies in a patient's spine. Derotation of the vertebral body with derotation apparatus 10 may also straighten curvature of the spine. In an embodiment, derotation apparatus 10 may be used in conjunction with an implant (e.g., a bone fastener coupled to a rod) to also address curvature of the spine. An embodiment of treating a spinal irregularity may include coupling derotation apparatus 10 to an implant. In an embodiment, the implant may be attached to a vertebral body. Coupling derotation apparatus 10 to an implant may include, for example, placement of distal end 70 of inner sleeve 50 over implant. In an embodiment, distal end 70 may be placed over implant to prevent separation of inner sleeve from implant. Coupling derotation apparatus 10 to implant further may include placing tube assembly 20 into a locked position to further secure inner sleeve 50 onto implant. In an embodiment, in the locked position, outer sleeve 60 may be disposed over distal end 70 of inner sleeve 50, clamping distal end 70 onto the implant. After securing the inner sleeve 50 on the implant, force may be applied to handle assembly 40 to derotate the vertebral body to which the implant is attached.

Embodiments for treating a spinal irregularity further may include coupling derotation apparatus 10 to at least one additional derotation apparatus 10 to form a coupled derotation system 225. For example, ball joints 80 in separate derotation apparatus 10 may be aligned so that a coupling rod 220 may be placed into a corresponding clamp 300 of the aligned ball joints 80. To lock the coupling rod 220 in place, the aligned ball joints 80 may then be placed in a locked position, for example, by tightening of a corresponding handle assembly 40. It should be understood that each derotation apparatus 10 in coupled derotation system 225 may be coupled to a corresponding implant. Force may be applied to handle assembly 40 in at least one derotation apparatus 10 in coupled derotation system 225. In an embodiment, force may be applied to handle assembly 40 of each derotation apparatus 10 in coupled derotation system 225. Application of force to handle assembly 40 should derotate the vertebral bodies to which coupled derotation system 225 is attached.

Figure 12:
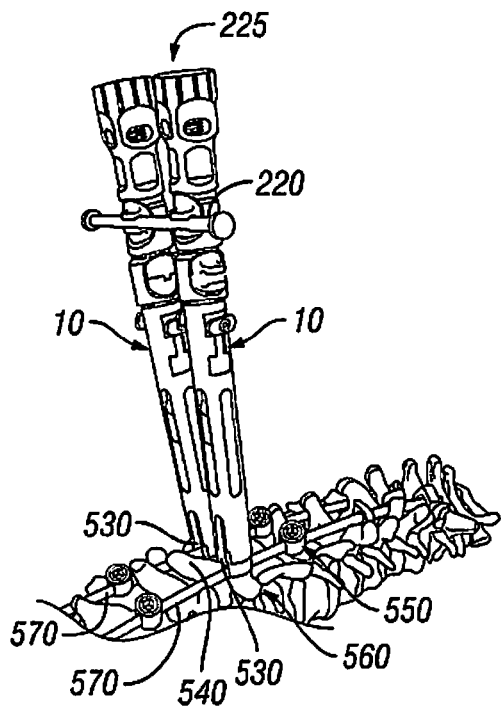
FIG. 12 illustrates an embodiment of a coupled derotation system with two derotation apparatuses attached on either side of the same vertebral body.

Referring now to FIG. 12, coupled derotation system 225 for treatment of spinal irregularities is illustrated in accordance with one embodiment of the present invention. As illustrated, coupled derotation system 225 includes two derotation apparatuses 10 interconnected by coupling rod 220. In the illustrated embodiment, derotation apparatuses 10 are connected to bone fasteners 530 on either side of vertebral body 540. Rotational force applied to vertebral body 540 should be distributed between bone fasteners 530. As illustrated, bone fasteners 530 may be a component of a bone fixation system 550 for fusing spine 560 that may include a single rod or a pair of parallel rods 570.

Figure 13:
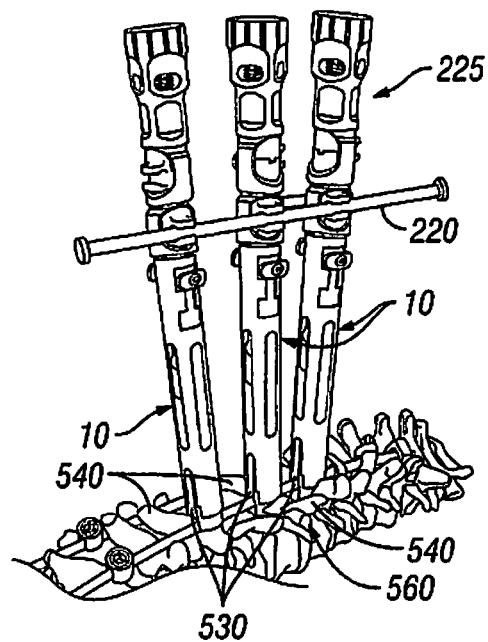
FIG. 13 illustrates an embodiment of a coupled derotation system with three derotation apparatuses in an inline arrangement.

Referring now to FIG. 13, an embodiment of coupled derotation system 225 for treatment of spinal irregularities is illustrated in which three derotation apparatuses 10 interconnected by coupling rod 220 are connected to bone fasteners 530 on the same side of spine 560. In an embodiment, derotation apparatuses 10 may be connected to vertebral bodies 540 at the apex of the curvature of spine 560. This arrangement of derotation apparatuses 10 should distribute force across multiple levels of spine 560.

Figure 14:
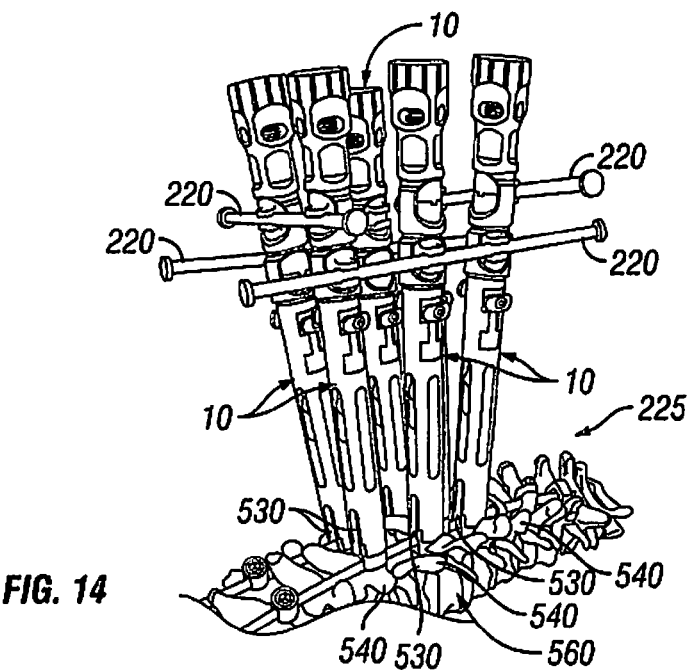
FIG. 14 illustrates an embodiment of a coupled derotation system with multiple derotation apparatuses.

Referring now to FIG. 14, an embodiment of coupled derotation system 225 for treatment of spinal irregularities is illustrated in which multiple derotation apparatuses 10 are interconnected by coupling rods 220. As illustrated, derotation apparatuses 10 may be coupled to bone fasteners 530 over multiple levels of spine 560 and on both sides of spine 560. This arrangement of derotation apparatuses 10 should distribute force across multiple levels of spine 560 for derotation of vertebral bodies 540.

While it is apparent that the invention disclosed herein is well calculated to fulfill the objects stated above, it will be appreciated that numerous modifications and embodiments may be devised by those skilled in the art.

What is claimed is:

1. A method for treating a spinal irregularity:
   providing a first derotation apparatus comprising a ball joint assembly having a first ball joint and a second ball joint that articulates independently of the first ball joint;
   providing a second derotation apparatus comprising a ball joint assembly;
   coupling the first derotation apparatus to a first implant coupled to a vertebral body;
   coupling the second derotation apparatus to a second implant coupled to a vertebral body;
   aligning the ball joint assembly of the first derotation apparatus and the ball joint assembly of the second derotation apparatus with one another;
   coupling a first rod between one of the first and second ball joints of the ball joint assembly of the first derotation apparatus and the ball joint assembly of the second derotation apparatus to interconnect the first derotation apparatus and the second derotation apparatus; and
   coupling a second rod to the other of the first and second ball joints of the ball joint assembly of the first derotation apparatus,
   wherein at least one of the first ball joint and the second ball joint of the first derotation apparatus comprises an upper portion and a lower portion that match together to form a rotatable ball, the upper portion comprising a radially extending upper tab, the lower portion comprising a radially extending lower tab, and the upper tab and the lower tab forming a clamp for receiving the first or second rod.

2. The method of claim 1, wherein the first implant and the second implant are secured on either side of the same vertebral body.

3. The method of claim 1, wherein the first implant and the second implant are secured on the same side of a spine.

4. The method of claim 1, further comprising: providing a third derotation apparatus comprising a ball joint assembly; and coupling the first rod to the ball joint assembly of the third derotation apparatus to interconnect the first derotation apparatus, the second derotation apparatus, and the third derotation apparatus.

5. The method of claim 1, further comprising: providing a third derotation apparatus comprising a ball joint assembly; and coupling the second rod between the ball joint assembly of the third derotation apparatus with the-a second ball joint of the first derotation apparatus.

6. The method of claim 1, comprising tightening a handle assembly of the first derotation apparatus to secure the first rod in a clamp of the ball joint assembly of the first derotation apparatus.

7. The method of claim 1, wherein the first derotation apparatus comprises a tube assembly that comprises an inner sleeve and an outer sleeve, and wherein coupling the first derotation apparatus to the first implant comprises placing a distal end of the inner sleeve over the implant and sliding the outer sleeve over the distal end of the inner sleeve.

8. The method of claim 1, wherein the ball joint assembly of the second derotation apparatus has a first ball joint and a second ball joint that articulates independently of the first ball joint.

9. The method of claim 1, wherein one or both of the first and second derotation apparatus further comprises:
   a tube assembly comprising an inner sleeve and an outer sleeve disposed over the inner sleeve, wherein the inner sleeve has a distal end for attachment to the implant;
   a handle assembly; and
   the ball joint assembly disposed between the tube assembly and the handle assembly.

10. A method for treating a spinal irregularity:
   providing a first derotation apparatus comprising a ball joint assembly having a first ball joint and a second ball joint that articulates independently of the first ball joint;
   providing a second derotation apparatus comprising a ball joint assembly;
   coupling the first derotation apparatus to a first implant coupled to a vertebral body;
   coupling the second derotation apparatus to a second implant coupled to a vertebral body;
   aligning the ball joint assembly of the first derotation apparatus and the ball joint assembly of the second derotation apparatus with one another;
   coupling a first rod between one of the first and second ball joints of the ball joint assembly of the first derotation apparatus and the ball joint assembly of the second derotation apparatus to interconnect the first derotation apparatus and the second derotation apparatus wherein one or both of the first and second ball joints comprises an upper portion and a lower portion that match together to form a rotatable ball, the upper portion comprising a radially extending upper tab, the lower portion comprising a radially extending lower tab, and the upper tab and the lower tab forming a clamp for receiving the first rod; and coupling a second rod to the other of the first and second ball joints of the ball joint assembly of the first derotation apparatus.

11. The method of claim 10, wherein the first implant and the second implant are secured on either side of the same vertebral body.

12. The method of claim 10, wherein the first implant and the second implant are secured on the same side of a spine.

13. The method of claim 10, further comprising: providing a third derotation apparatus comprising a ball joint assembly; and coupling the first rod to the ball joint assembly of the third derotation apparatus to interconnect the first derotation apparatus, the second derotation apparatus, and the third derotation apparatus.

14. The method of claim 10, further comprising: providing a third derotation apparatus comprising a ball joint assembly; and coupling the second rod between the ball joint assembly of the third derotation apparatus with the second ball joint of the first derotation apparatus.

15. The method of claim 10, comprising tightening a handle assembly of the first derotation apparatus to secure the first rod in a clamp of the ball joint assembly of the first derotation apparatus.

16. The method of claim 10, wherein the first derotation apparatus comprises a tube assembly that comprises an inner sleeve and an outer sleeve, and wherein coupling the first derotation apparatus to the first implant comprises placing a distal end of the inner sleeve over the implant and sliding the outer sleeve over the distal end of the inner sleeve.

* * * * *